United States Patent [19]
Grasset et al.

[11] Patent Number: 6,165,491
[45] Date of Patent: Dec. 26, 2000

[54] PHARMACEUTICAL COMPOSITION BASED ON ESTROGEN AND PROGESTERONE

[75] Inventors: Etienne Grasset, Boulogne; Didier Terracol, Verrieres le Buisson, both of France; Javier Gil Galdona, Madrid, Spain

[73] Assignee: Effik SCA BAT, France

[21] Appl. No.: 09/128,324

[22] Filed: Aug. 3, 1998

[30] Foreign Application Priority Data

Apr. 27, 1998 [FR] France .................................. 98 05262

[51] Int. Cl.$^7$ .............................. A61F 6/06; A61F 13/02; A61K 9/48
[52] U.S. Cl. .......................... 424/430; 424/434; 424/451
[58] Field of Search .................................. 424/430, 451, 424/434

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,383,993 | 5/1983 | Hussain et al. . |
| 4,418,068 | 11/1983 | Jones . |
| 4,447,620 | 5/1984 | Sih et al. . |
| 4,847,276 | 7/1989 | Yarrington . |
| 4,900,734 | 2/1990 | Maxson et al. . |
| 5,075,321 | 12/1991 | Schreiber . |
| 5,391,557 | 2/1995 | Cullinan et al. . |
| 5,441,965 | 8/1995 | Sall et al. . |
| 5,445,941 | 8/1995 | Yang . |
| 5,476,862 | 12/1995 | Calnek et al. . |
| 5,482,949 | 1/1996 | Black et al. . |
| 5,508,292 | 4/1996 | Sall et al. . |

FOREIGN PATENT DOCUMENTS

| | | |
|---|---|---|
| 0393539 | 10/1990 | European Pat. Off. . |
| 0461290 | 12/1991 | European Pat. Off. . |
| 0 521 381 A1 | 6/1992 | European Pat. Off. . |
| 0 878 195 | 11/1998 | European Pat. Off. . |
| 2747042 | 10/1997 | France . |
| WO93/10113 | 6/1993 | Japan . |
| WO93/1074 | 6/1993 | WIPO . |
| 9422426 | 10/1994 | WIPO . |
| WO 98/47365 | 4/1997 | WIPO . |
| 9740823 | 11/1997 | WIPO . |

OTHER PUBLICATIONS

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am. Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;" Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109; 1981, 987–989.

Black, L.J. "Biological Actions and Binding Properties of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

(List continued on next page.)

*Primary Examiner*—Carlos A. Azpuru
*Attorney, Agent, or Firm*—Bierman, Muserlian and Lucas

[57] ABSTRACT

A pharmaceutical composition, intended for menopausal replacement therapy, comprising a suspension of progesterone in a lipophilic medium solution of a 17-estradiol salt in the lipophilic medium, the weight ratio of progesterone to the base 17-estradiol being 25 to 600.

13 Claims, No Drawings

OTHER PUBLICATIONS

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxy]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Dina M. Bitar et al., Suppression of Experimental Autoimmune Encephalomyelitis by the Oral Administration of Myelin Basic Protein, Cellular Immunology 112, 364–370, 1988.

Paul J. Higgins, et al., Suppression of Experimental Autoimmune Encephalomyelitis by Oral Adminstration of Myelin Basic Protein and its Fragments, The Journal of Immunology, vol. 140(2), 440–445, Jan. 15, 1988.

Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor $\beta$, Intrerleukin 4, and Prostaglandin E Expression In the Brain, J. Exp. Med. vol., 176, 1355–1364, Nov. 1992.

C.D. Jones, et al. Antiestrogens. 2.[1] Structure–Activity Studies in a Series of 3–Aroyl–2–arylbenzo{b}thien–3–yl][4–[2–(1–piperidinyl)ethoxy]–phenyl]methanone Hydrochloride (LY156758), A remarkably Effective Estrogen Antagonist With Only Minimal Intrinsic Estrogenicity, J. Med. Chem., 1984, 27, 1057–1066.

A Hendrick, et al., Tamoxifen and Thromboembolism, Journal of the American Medical Association, vol. 243, No. 6, Feb. 8, 1980.

Radwanska, E., The Role of Reproductive Hormones in Vascular Diseases and Hypertension, Steroids, 58(12), 605, Dec. 1993.

Pfilger, et al., Acta Med. Austriaca, 18(3), 68–72, 1991.

Database HCAPLUS on STN, AN 1988:32668, "Evidence that transforming growth factor–beta is a hormonally regulated negative growth factor in human breast cancer cells". Cell, (Cambridge, Mass.) 1987, 48(3), 417–428.

PHARMACEUTICAL COMPOSITION BASED ON ESTROGEN AND PROGESTERONE

The present invention relates to a composition, based on progesterone and estrogen, which is intended for menopausal hormone replacement therapy.

STATE OF THE ART

The use of estroprogestative hormone replacement therapy (HRT) for post-menopausal hormone deficiency is widespread in Europe, in particular, and continues to increase. This development is due to several factors: 1) demographic changes, 2) increased life expectancy, which makes it more and more necessary, 3) increasingly numerous demonstrations of its very varied beneficial effects and 4) the development of therapeutic protocols in terms of doses and rates of administration, allowing the minimum effective dose to be administered, thus avoiding or minimizing deprivation-hemorrhaging and the endometrial risk factor.

The hormonal cycle in women is essentially due to the production of two hormones, 17-estradiol [(17)-estra-1,3,5 (10)-trieno-3,17-diol] and progesterone [Δ4-pregnen-3,20-dione]. In the case of a deficient cycle, particularly during menopause when the endogenous production of the two hormones decreases, it is customary to compensate for this deficiency by exogenously supplying these two hormones, which is defined as hormone replacement therapy.

Menopausal hormone replacement therapy involves the administration of an estrogen which can be administered via different routes, particularly oral or transdermal routes. The substances used in the case of oral administration are either the natural hormone (17-estradiol) or 17-estradiol valerate, which are generally micronized, or equine conjugate derivatives, or different derivatives (estriol, estrone). The most common daily doses of estrogens range from 1 to 2 mg of estradiol or from 1 to 2 mg of 17-estradiol valerate (which corresponds to 0.76 and 1.53 mg of base estradiol, respectively), whereas, for the equine conjugate derivatives, the daily doses range from 0.625 mg to 1.250 mg. The long-term efficacy of lower oral doses of estrogen has not been demonstrated with certainty. (Rozenbaum: Estrogens in: Clinical Pharmacology: Giroud MahÈ, Meyniel. Eds. Expansion Scientifique Franaise, Paris, 1988, 2075–2092).

The sustained and isolated systemic administration of estrogens increases the risk of endometrial hyperplasia. The occurrence of an atypical hyperplasia exposes women to an increased risk of cancer of the endometrium. To reduce this risk, it is customary to accompany the estrogen treatment by a progestative treatment. For this complementary treatment, it is possible to use synthetic progestatives or the natural hormone (progesterone), and preferably the latter, since its metabolism provides additional advantages: since progesterone has no androgenic effect, it does not induce a lowering of the level of certain lipoproteins such as, for example, HDL-cholesterol (Bolaji, Grimes, Mortimer, Tallon, Fottrell, O'Dwyer: Low dose progesterone therapy in estrogenized postmenopausal women: effects on plasma lipids, lipoproteins and liver function parameters, Eur. J. Obstet. Gynaecol. Reprod. Biol. 1993, 48: 61-8; and The Writing Group For the Pepi Trial: Effects of estrogen/progestin regimens on heart disease risk factors in postmenopausal women, Jama, 1995, 273: 195–208).

For the oral administration of progesterone, the doses usually used in menopausal hormone replacement therapy range from 100 to 300 mg per day. These doses allow the endometrium to be effectively protected (Darj, Nilsson, Axelsson, Hellberg: Clinical and endometrial effects of estradiol and progesterone in postmenopausal women, Maturitas, 1991, 13: 109-15; and Faguer, Gillet, AndrÈ, Philippe: AmÈnorrhÈe lors du traitement hormonal substitutif de la mÈnopause par association estradiol percutanÈet de progestÈrone orale micronisÈe [Amenorrhoea during menopausal hormone replacement therapy by the combination of percutaneous estradiol and micronized oral progesterone], Contracep. Fertil. Sex., 1993, 231: 849–52; and Moyer, De Lignieres, Driguez, Pez: Prevention of endometrial hyperplasia by progesterone during long term estradiol replacement: influence of bleeding pattern and secretory changes, Fertil Steril., 1993, 59: 992-7).

Moreover, it is known that the use of micronized progesterone suspended in an oily excipient improves its oral absorption (Hargrove, Maxon, Colston, Wentz: Absorption of oral progesterone is influenced by vehicle and particle size, Am. J. Obstet. Gynaecol., 1989, 161: 948–51). Under these conditions, it has been possible to obtain effective progesterone concentrations in the target organs (Morville, Dray, Reynier, Barrat: BiodisponibilitÈ de la progestÈrone naturelle administrÈe par voie orale, Mesure des concentrations du steroide dans le plasma, endometre et le tissue mammaire [Bioavailability of orally-administered natural progesterone. Measurement of the concentrations of the steroid in the plasma, the endometrium and mammary tissue], J. Gyn. Obstet. Biol. Reprod., 1992, 11: 355–63).

Soft capsules for oral or vaginal administration of micronized natural progesterone suspended in groundnut oil are available on the market, such as, for example, the capsules sold by Laboratoires Besins-Iscovesco in France, under the brand name Utrogestan.

The difficulty of manufacturing a medicinal product which combines the two hormones at the desired doses (progesterone and 17-estradiol or a salt or a derivative of this salt) in a single pharmaceutical form demands that the usual hormone replacement therapy for menopause should comprise the administration of two different medicinal products, one supplying the estrogen and the other supplying the progesterone or another progestative agent.

The use of two separate medicinal products for treating menopause increases the cost of the treatment, affects its satisfactory use and carries a certain inherent risk of the treatment not being properly adhered to, which can give rise to a decrease in the therapeutic efficacy expected of the treatment.

OBJECTS OF THE INVENTION

It is an object of the invention to provide menopausal hormone compositions comprising a suspension of progesterone in a lipophilic medium solution of a 17-estradiol salt, the weight ratio of progesterone to estradiol salt being 25 to 600 and a process for its preparation.

It is another object of the invention to provide a novel menopausal hormone replacement method.

These and other objects and advantages of the invention will become obvious from the following detailed description.

THE INVENTION

The combination of the two hormones in a single pharmaceutical form is a safety factor and guarantees correct adherence to the treatment, since it becomes physically impossible for the patient to take the estrogen alone without its corresponding progestative complement. It is possible to prepare a medicinal product containing the two hormones in a single pharmaceutical form which releases these hormones into the body in an equilibrated manner.

Medicinal products based on progesterone and estradiol have already been proposed—see FR-A-2,747,042—which consists of introducing a suspension of progesterone in the micronized state into a medium based on oil and estradiol, while still preventing the estradiol from dissolving, even partially, in the oil. It envisages enclosing the estradiol in a microsphere consisting of a polymer which is insoluble in the oil and soluble in the biological medium. This type of composition is not entirely satisfactory and in particular, poses problems of heterogeneity due to the different particle sizes and densities of the active substances present in particulate form.

Oral preparations, packaged in soft gelatin capsules, containing estradiol valerate dissolved in a physiologically acceptable lipophilic medium, such as a plant oil, are also known from EP-A-0,393,539. That patent observes that this form of preparation leads to higher bioavailability and an accelerated release of the active substance. It envisages the use of a composition containing, in dissolved form, estradiol valerate and a progestative agent in a proportion of 5 mg/1 mg of the estrogen also dissolved in the lipophilic medium.

Application WO 97/40823 relates to compositions which can contain progesterone, estradiol and also testosterone and also proposes using the active substances in a form which is dissolved in the medium and, to this end, uses a combination of a lipophilic surfactant and a hydrophilic surfactant which are capable of improving the solubilization of the estrogen and of the progesterone in a lipophilic medium. The maximum progesterone concentration in a medium containing no alcohol is 4.5%.

It has been discovered that it is possible to provide patients requiring a menopausal hormone replacement therapy, with a composition comprising an estrogen dissolved in the lipophilic medium of a progesterone suspension.

It has been observed, particularly that this combination makes it possible to administer the progesterone and the estrogen simultaneously while at the same time maintaining the equilibrium between the estrogen and progesterone which is necessary for an effective menopausal hormone replacement therapy, i.e. one which releases the estrogen and progesterone in the desired relative proportions. Treatment with the combination of the invention makes it possible to replace the natural hormones and to reduce hot flushes, genitourinary disorders and the risks of osteoporosis, while at the same time effectively protecting the endometrium.

It has also been discovered that the total solubilization of the estradiol salt in the medium of the progesterone suspension makes it possible to obtain a slower release of estradiol, because of the relatively high proportion of progesterone in particulate form, this release thus being sustained over time, in contrast with prior art deductions.

The composition of the invention, which is intended to be used in menopausal hormone replacement therapy, comprises a suspension of progesterone in a lipophilic medium and a 17-estradiol salt dissolved in the lipophilic medium, the ratio of the weight of progesterone to the weight of corresponding base 17-estradiol being between 25 and 600.

In accordance with the invention, 17-estradiol valerate is preferably used. The progesterone is preferably used in micronized form, the particle sizes generally being between 1 and 100 microns, and more preferably, between 1 and 50 microns. The progesterone is essentially in suspension, although there may be a relatively small proportion, generally not exceeding 5%, possibly dissolved in the lipophilic medium. The estrogen must be completely dissolved in the lipophilic medium.

The lipophilic medium consists of oils, preferably of plant origin, usually used in pharmaceutical formulations, such as groundnut oil, sesame oil, soybean oil or fractionated coconut oil.

A surfactant can be added to the medium, particularly amphoteric surfactants such as soybean lecithin. These surfactants can be used in proportions of from 0.05 to 5% by weight relative to the weight of oil.

The compositions of the invention preferably contain between 50 and 300 mg of progesterone in suspension and from 0.5 to 2 mg of base 17-estradiol (in the form an estradiol salt, particularly 17-estradiol valerate).

The compositions of the invention are prepared by, in a first step, dissolving the estrogen in the lipophilic medium and then the progesterone in the form of micronized particles is added to the lipophilic estrogen solution and the progesterone in particulate form is mixed with the said lipophilic estrogen solution.

In accordance with the invention, the estrogen is completely dissolved in the lipophilic medium with the progesterone essentially being in suspension.

It is possible to dissolve the estrogen, and more particularly the 17-estradiol valerate, completely, without the risk of recrystallization, in the lipophilic medium defined above, by heating the mixture to a temperature of between 30 and 50° C. and preferably to about 40° C.

The complete dissolution of the estrogen constitutes an important element of the invention, since the subsistence of estrogen particles in the presence of the progesterone particles could lead to problems of heterogeneity of the capsules, owing to the different dimensions and densities of the particles and the predominant presence of progesterone particles in the composition.

It has also been observed that the predominant presence of progesterone in particulate form in the composition contributes towards regularizing the kinetics of estrogen release, thereby allowing an equilibrated treatment to be provided.

The composition in accordance with the invention can be formulated in appropriate pharmaceutical forms which allow the suspension to be maintained in the lipophilic medium of the invention. The compositions can be formulated for oral or vaginal administration.

One specific and preferred preparation of the invention is a formulation in soft capsules which capsules are obtained by conventional techniques [Tratado de Farmacia Galenica, C. Fauli i Trillo, Luzan 5 S. A. de Ediciones, 1st Edition (1993), pages 497 et seq. and especially page 588–607]. These soft capsules can be made of gelatin or any other substance usually used to produce such soft capsules.

The compositions of the invention are used in menopausal hormone replacement therapy, which consists in administering a therapeutically effective amount of a composition of the invention to a potential patient. Therapeutically effective amount means the amount of the pharmaceutical composition which is sufficient to treat menopause. Active doses of from 0.5 to 2 mg/day of base 17-estradiol in the form of a 17-estradiol salt or derivative, particularly 17-estradiol valerate, and 50 to 300 mg/day of progesterone are generally used.

According to a preferred embodiment of the invention, soft capsules containing 100 mg of micronized progesterone and 1 mg of estradiol valerate, administered orally or vaginally once a day, are used. This dosage can, however, vary as a function of the pathology concerned, its severity, the duration of the treatment, the patient's age and weight and the relative efficacy of the composition.

By virtue of the invention, it is thus possible to simplify adherence to the therapy, to increase the efficacy and to allow an administration which is more convenient for the patient. The invention thus constitutes a guarantee of certainty of adherence to the treatment since it then becomes impossible for the patient to ingest the estrogen without the corresponding progestative dose.

In the following examples, there are described several preferred embodiments to illustrate the invention. However, it should be understood that the invention is not intended to be limited to the specific embodiments.

EXAMPLE 1

Preparation of soft capsules.

Preparation of the composition 1 mg of USP-grade [US Pharmacopoea, Volume XXIII (USP XXIII)] 17-estradiol valerate, supplied by AKZO Diosynth, was dissolved in a mixture of 149 mg of groundnut oil of European Pharmacopoea (EP) grade and 1 mg of soybean lecithin. 100 mg of EP-grade (European Pharmacopoea, Vol. III) micronized progesterone with a particle size of between 1 and 100 microns (supplied by AKZO Diosynth) were added to the solution and the solution was stirred until completely homogeneous.

Preparation of the soft capsules

Gelatin capsules each containing 251 mg of the oily solution above were filled according to conventional processes [Tratado de Farmacia Galenica, cited above]. The capsules were obtained from a mixture of gelatin, glycerol, opacifiers (titanium dioxide), dyes (quinoline and cuprosodic chlorophyll) and purified water and all of the ingredients were of EP grade.

EXAMPLES 2 TO 5

FORMULATIONS FOR "4 oval" CAPSULES

The capsules of "4 oval" format have a maximum capacity of 0.246 ml.

|  | 2 | 3 | 4 | 5 |
|---|---|---|---|---|
| Progesterone | 100 mg | 100 mg | 100 mg | 100 mg |
| Estradiol valerate | 1.00 mg | 1.50 mg | 1.87 mg | 2.14 mg |
| Base Estradiol | 0.79 mg | 1.18 mg | 1.47 mg | 1.69 mg |
| Groundnut oil | 149 mg | 149 mg | 149 mg | 149 mg |
| Soybean lecithin | 1.00 mg | 1.00 mg | 1.00 mg | 1.00 mg |

|  | 6 | 7 | 8 | 9 |
|---|---|---|---|---|
| Progesterone | 100 mg | 100 mg | 100 mg | 100 mg |
| Estradiol valerate | 1.41 mg | 2.11 mg | 2.63 mg | 3.01 mg |
| Base Estradiol | 1.11 mg | 1.66 mg | 2.07 mg | 2.37 mg |
| Groundnut oil | 210 mg | 210 mg | 210 mg | 210 mg |
| Soybean lecithin | 1.4 mg | 1.4 mg | 1.4 mg | 1.4 mg |

STUDY OF THE SOLUBILIZATION OF THE ESTRADIOL

The results were obtained using a 149 mg of oil solution and 1 mg of soybean lecithin (the solvent), with heating to +40∞ C.

| Ratio of estradiol valerate to solvent (w/w) | Amounts of estradiol valerate in 150 mg of solvent | Amount of base estradiol in 150 mg of solvent |
|---|---|---|
| 1/70 | 2.14 mg | 1.69 mg |
| 1/80 | 1.87 mg | 1.47 mg |
| 1/100 | 1.50 mg | 1.18 mg |
| 1/150 | 1.00 mg | 0.79 mg |

COMPARATIVE STUDY OF THE RATE OF RELEASE IN AQUEOUS MEDIUM OF ESTRADIOL VALERATE DISSOLVED IN VARIOUS LIPID MEDIA

The aqueous medium used was 100 ml of an aqueous solution containing 1% of sodium lauryl sulfate, maintained at 37° C. and stirred by rotation at 100 rpm.

Samples tested:

A. 5 mg of estradiol valerate in a composition in accordance with the invention, i.e. 750 mg of groundnut oil and 500 mg of micronized progesterone.

B. 5 mg of estradiol valerate in oil, i.e. 750 mg of oil. The estradiol was detected in aqueous solution by HPLC, u-pack C18 3.9×300 mm column, methanol/water mobil phases, reading by UV spectrometry at 280 nm.

Release of estradiol valerate in aqueous medium (Concentration as a % of the theoretical maximum of 5 mg/100 ml, average±SD of 6 measurements)

| Time (min) | A | B |
|---|---|---|
| 15 | 6.2 ± 1.2 | 12.7 ± 2.6 |
| 30 | 7.3 ± 0.9 | 18.4 ± 3.4 |
| 45 | 8.0 ± 1.5 | 19.2 ± 2.8 |
| 60 | 8.9 ± 1.4 | 20.7 ± 3.2 |

These results show that the addition of particles of progesterone slows down the release of the estradiol valerate in an aqueous medium, coming close to that of the digestive tract, and thus allows the bioavailability of the active substances to be controlled.

Various modifications of the compositions and method of the invention may be made without departing from the spirit or scope thereof and it is to be understood that the invention is intended to be limited only as defined in the appended claims.

What we claim is:

1. A pharmaceutical composition comprising a suspension of progesterone in a lipophilic medium containing 17-estradiol valerate dissolved in said lipophilic medium, the weight ratio of progesterone to the corresponding base of 17-estradiol base is 25 to 600.

2. A composition of claim 1 wherein the progesterone is in the form of micronized particles having a particle size of 1 to 100 microns.

3. A composition of claim 1 wherein the lipophilic medium is a plant oil.

4. A composition of claim 1 wherein the lipophilic medium also contains a surfactant.

5. A composition of claim 4, wherein the surfactant is an amphoteric surfactant.

6. A composition of claim 5, wherein the surfactant is a soybean lecithin.

7. A composition of claim 5 wherein the surfactant is present in proportions of 0.5 to 5% by weight relative to the weight of oil.

8. A composition of claim 1 containing from 50 to 300 mg of progesterone in particulate form and 0.5 to 2 mg, expressed as base 17-estradiol, in the form of 17-estradiol valerate.

9. A process for preparing a composition of claim 1 wherein in a first stage, the 17-estradiol valerate is dissolved in a lipophilic medium and the progesterone then is added in particulate form and is mixed with the lipophilic estrogen solution.

10. The process of claim 9 wherein the mixture of estradiol valerate and of lipophilic medium is heated to a temperature to bring about complete dissolution of the estradiol valerate.

11. A menopausal hormone replacement composition formulated for oral or vaginal administration and containing an effective amount of a composition of claim 1.

12. A medicinal product of claim 11 in the form of a soft capsule intended for oral or vaginal administration.

13. A method of treating a female human for menopausal hormone deficiency comprising administering to a female human in need thereof an amount of a composition of claim 1 sufficient to relieve said deficiency.

* * * * *